(12) United States Patent
Amiri (10) Patent No.: US 9,532,911 B2
(45) Date of Patent: Jan. 3, 2017

(54) DISPOSABLE DIAPER WITH INTEGRATED DISPOSAL AID

(71) Applicant: Mamon Amiri, Redondo Beach, CA (US)

(72) Inventor: Mamon Amiri, Redondo Beach, CA (US)

( * ) Notice: Subject to any disclaimer, the term of this patent is extended or adjusted under 35 U.S.C. 154(b) by 0 days.

(21) Appl. No.: 14/964,161

(22) Filed: Dec. 9, 2015

(65) Prior Publication Data

US 2016/0101004 A1  Apr. 14, 2016

Related U.S. Application Data

(63) Continuation-in-part of application No. 14/220,141, filed on Mar. 20, 2014, now Pat. No. 9,283,126.

(51) Int. Cl.
| | |
|---|---|
| *A61F 13/15* | (2006.01) |
| *A61F 13/551* | (2006.01) |
| *A61F 13/84* | (2006.01) |
| *A61F 13/512* | (2006.01) |

(52) U.S. Cl.
CPC ....... *A61F 13/5519* (2013.01); *A61F 13/5512* (2013.01); *A61F 13/512* (2013.01); *A61F 2013/55125* (2013.01); *A61F 2013/8402* (2013.01)

(58) Field of Classification Search
CPC .............. A61F 2013/55125; A61F 13/5512
USPC .......... 604/385.06, 385.13, 385.3, 385.19
See application file for complete search history.

(56) References Cited

U.S. PATENT DOCUMENTS

| | | | | |
|---|---|---|---|---|
| 5,304,158 A | * | 4/1994 | Webb | A61F 13/551 604/385.13 |
| 2004/0092901 A1 | * | 5/2004 | Reece | A61F 13/84 604/385.06 |

* cited by examiner

*Primary Examiner* — Jacqueline Stephens (57) ABSTRACT

A disposable diaper includes a disposal aid coupled with an exterior surface of a waistband region of the diaper. The disposal aid includes a base, a first removable cover and a second removable cover. A disposal bag is placed on the base and covered by the first removable cover. A cleaning wipe is place on the first removable cover and covered by the second removable cover. The base may include a cavity to receive the disposal bag so as to reduce the overall height of the disposal aid. The disposal aid may alternatively be configured to include a disposal bag encased in a casing and a cleaning wipe, both of which are placed on the base of the disposal aid and covered by a single removable cover.

20 Claims, 8 Drawing Sheets

DISPOSABLE DIAPER WITH INTEGRATED DISPOSAL AID

CROSS REFERENCE TO RELATED APPLICATIONS

The present patent application is a continuation-in-part of a co-pending non-provisional patent application entitled "DISPOSABLE DIAPER WITH INTEGRATED DISPOSAL AID," filed Mar. 20, 2014, as U.S. patent application Ser. No. 14/220,141 by the same inventor. This patent application claims the benefit of the filing date of the cited non-provisional patent application according to the statutes and rules governing provisional and non-provisional patent applications, particularly 35 USC §§119, 120, 121, and 37 CFR §1.78. The specification and drawings of the cited non-provisional patent application are specifically incorporated herein by reference.

COPYRIGHT

A portion of the disclosure of this patent document contains material which is subject to copyright protection. The owner has no objection to the facsimile reproduction by anyone of the patent disclosure, as it appears in the Patent and Trademark Office files or records, but otherwise reserves all copyright rights whatsoever.

FIELD OF INVENTION

The present invention relates to baby care products, particularly wearable diapers. A disposable diaper including a disposal aid which is coupled with a diaper so as to provide a means for cleaning the wearer and disposing the diaper. In particular, the disposal aid includes a base and one or more removable covers for containing a cleaning wipe and a disposal bag.

BACKGROUND

The use of disposable diapers is widespread in the U.S. as well as many other countries. The typical baby goes through 5000 to 8000 diapers before the completion of potty training, and Americans use millions of diapers each year. Obviously, the mess and odor associated with diapers is undesirable and a source of discomfort in the household. Disposable diapers are often thrown directly into the trash, resulting, in an emanating odor in the trash bin. Alternatively, to avoid this, the user must place the dirty diaper in some type of bag prior to placing it in the trash. This however, is inconvenient in that it requires the user to have a supply of such bags and retrieve the bag when needed. Similarly, cleaning wipes are a common tool in cleaning the baby upon unfastening or removal of the diaper, and the user must have a supply of such wipes nearby when needed. There is a need in the art for a disposable diaper that is more amenable to convenient cleanup and disposal.

SUMMARY

In one aspect, a disposable diaper is disclosed wherein the diaper comprises a diaper body comprising a waistband region, a disposal aid coupled with an exterior surface of the waistband region, said disposal aid, comprising a base operable to contain a cleaning wipe and a disposal bag, a first removable cover removably affixed to the base and operable to cover the disposal bag and to facilitate a platform to place the cleaning wipe thereon, and a second removable cover removably affixed to the first removable cover and operable to cover the cleaning wipe, wherein by removing the second removable cover, the cleaning wipe becomes accessible, thereby, facilitating removal of the cleaning wipe, and wherein by removing the first removable cover, the disposal bag becomes accessible, thereby, facilitating removal of the disposal bag.

Preferably, the disposal aid is coupled with the exterior surface of the waistband region via an adhesive.

Preferably, the disposal aid is coupled with the exterior surface of the waistband region and disposed about a centerline of the disposable diaper.

Preferably, the base is made of polyethylene.

Preferably, the base is rectangular.

Preferably, the first removable cover and the second removable cover are rectangular.

Preferably, the base comprises a cavity operable to receive the disposal bag within said cavity, thereby reducing an overall height of the disposal aid.

Preferably, the first removable cover includes a first tab affixed to a distal edge of the first removable cover thereby facilitating easy removal of the first removable cover, and wherein the second removable cover includes a second tab affixed to a distal edge of a perforated section of the second removable cover and an elliptical perforation around the perforated section, thereby facilitating easy removal of the perforated section of the second removable cover.

In another aspect, a disposable diaper is disclosed wherein the diaper comprises a diaper body comprising a waistband region, a disposal aid coupled with an exterior surface of the waistband region, said disposal aid, comprising a base operable to contain a cleaning wipe and a disposal bag, a casing operable to encase the disposal bag, and a removable cover removably affixed to the base and operable to cover the casing and the cleaning wipe, wherein by removing the removable cover, the casing and the cleaning wipe become accessible, thereby, facilitating removal of the casing and the cleaning wipe.

Preferably, the base is rectangular.

Preferably, the removable cover is rectangular.

Preferably, the base comprises a cavity operable to receive the disposal bag and the cleaning wipe within said cavity, thereby reducing an overall height of the disposal aid.

Preferably, the removable cover includes a tab affixed to a distal edge of the first removable cover thereby facilitating easy removal of the first removable cover.

In another aspect, a disposal aid configured to be coupled with an exterior surface of a diaper is disclosed wherein the disposal aid comprises a base operable to contain a cleaning wipe and a disposal bag, a first removable cover removably affixed to the base and operable to cover the disposal bag and to facilitate a platform to place the cleaning wipe thereon, and a second removable cover removably affixed to the first removable cover and operable to cover the cleaning wipe, wherein by removing the second removable cover, the cleaning wipe becomes accessible, thereby, facilitating removal of the cleaning wipe, and wherein by removing the first removable cover, the disposal bag becomes accessible, thereby, facilitating removal of the disposal bag.

Preferably, the base is rectangular.

Preferably, the first removable cover and the second removable cover are rectangular.

Preferably, the base comprises a cavity operable to receive the disposal bag within said cavity, thereby reducing an overall height of the disposal aid.

Preferably, the first removable cover includes a first tab affixed to a distal edge of the first removable cover thereby facilitating easy removal of the first removable cover, and wherein the second removable cover includes a second tab affixed to a distal edge of a perforated section of the second removable cover and an elliptical perforation around the perforated section, thereby facilitating easy removal of the perforated section of the second removable cover.

In another aspect, a disposal aid configured to be coupled with an exterior surface of a diaper is disclosed wherein the disposal aid comprises a base operable to contain a cleaning wipe and a disposal bag, a casing operable to encase the disposal bag, and a removable cover removably affixed to the base and operable to cover the casing and the cleaning wipe, wherein by removing the removable cover, the casing and the cleaning wipe become accessible, thereby, facilitating removal of the casing and the cleaning wipe.

Preferably, the base comprises a cavity operable to receive the disposal bag and the cleaning wipe within said cavity, thereby reducing an overall height of the disposal aid.

DETAILED DESCRIPTION OF THE PRESENTLY PREFERRED EMBODIMENTS

A patentably distinct disposable diaper is presented in this continuation-in-part application which complements the disposable diaper disclosed in the parent application. The present invention provides a different configuration of the disposable diaper where a disposal aid includes one or more removable covers for ease of access to its content, namely a disposal bag and a cleaning wipe. Additionally, the disposal aid includes a base where it can couple with the body of the diaper via an adhesive or other means of connection, such as Velcro or stitches. In the following, the text of the parent application will be repeated so as to give context to the disclosure. However, the present invention relates to what is disclosed starting with the description of FIG. 5. Furthermore, although in the parent and the present disclosures, the word "disposable" and "disposal" are used, the distinction is only contextual and that their construction should not differ.

Figure 1:
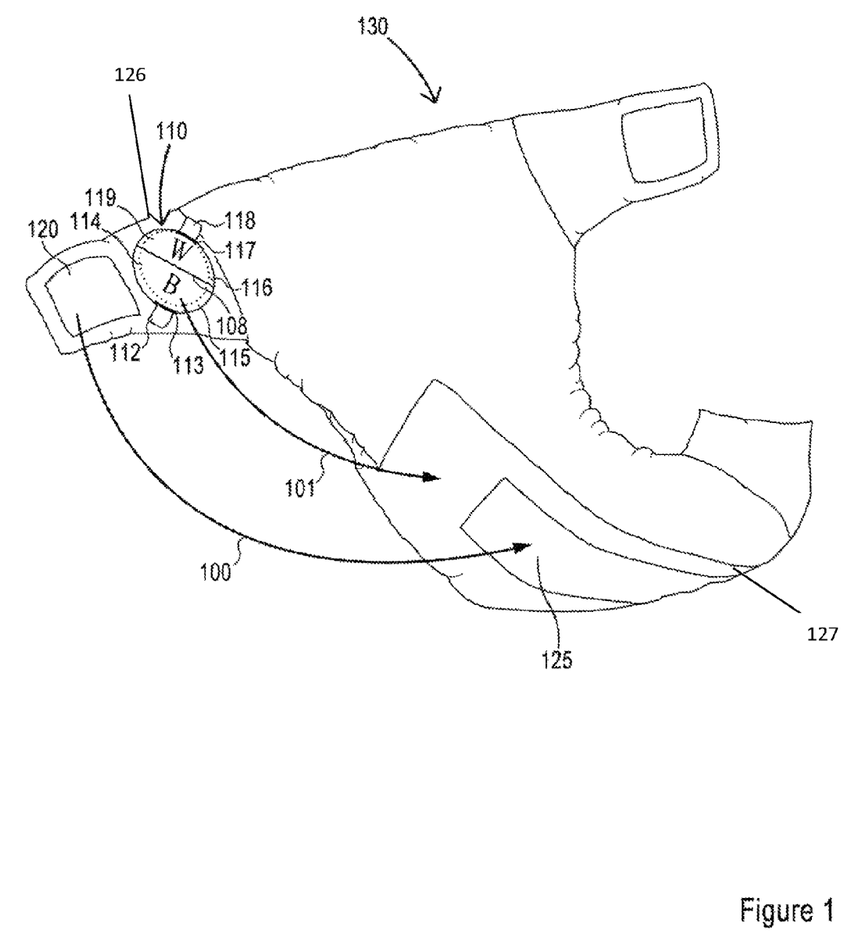
FIG. 1 illustrates a perspective view of the inside of the disposable diaper showing the configuration and position of the cleanup and disposal aid.

The present invention provides a disposable diaper with an integrated cleanup and disposal aid (i.e. "disposal aid") that allows for quick, convenient and sanitary clean up and disposal of the diaper. FIG. 1 illustrates a perspective view of the disposable diaper 130 ("diaper") of the present invention, including a diaper disposal aid 110 affixed to the waistband section of the diaper (i.e. rear end/upper section of the diaper). The overall configuration of the diaper is representative of a typical disposable diaper, which includes a waistband section 126, a crotch section 127, an upper fastening element 120 corresponding to the waistband section, and a lower fastening element 125 corresponding to the crotch area 127. The diaper disposal aid 110 comprises a bag compartment 115 with a disposal bag 114 contained therein (denoted by "B"), and a cleaning wipe compartment 116 (i.e. "wipe compartment") with a disposable cleaning wipe 119 contained therein (denoted by "W"). As shown, the waistband section 126 generally corresponds to the upper portion of the diaper, or the "rear" of the diaper as worn. Similarly, the crotch section 127 generally corresponds to the lower portion of the diaper, or the "front" of the diaper as worn. Thus, the terms "rear" and "frontal" maybe used herein to refer to the upper and lower portions of the diaper as shown in FIG. 1, respectively.

Figure 2:
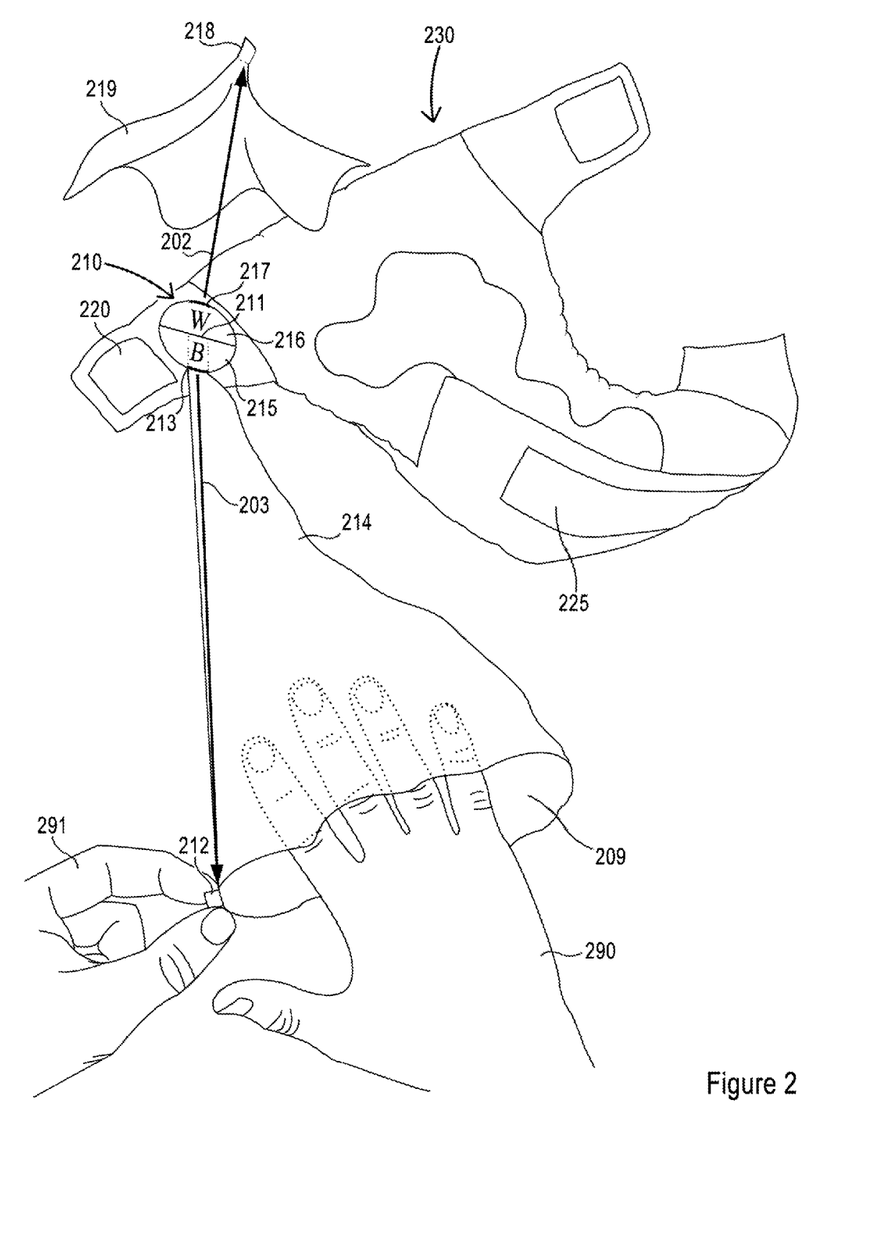
FIG. 2 illustrates a perspective view of the inside of the disposable diaper showing the removal of the cleaning wipe and the disposal bag from their respective containment pouches.

While the representation of the disposal aid 110 in FIG. 1 is that of a circular pouch partitioned into two semispherical compartments, other shapes could be used (e.g. a rectangular pouch partitioned into two rectangular compartments). The cleanup wipe (i.e. "wipe") allows for cleaning of the baby upon opening or removal of the diaper. The disposal bag 114 is used to dispose of the diaper after use. Both the disposal bag and the cleaning wipe are shown with dotted lines, as they lie within their respective pouches and are not visible in this view. The disposal aid 110 is a circular pouch partitioned into two adjoining pouches or compartments, separated by a divider 108. The bag compartment 115 further comprises a bag pull tab 112 and a bag extraction slit 113. The wipe compartment 116 further comprises a wipe pull tab 118 and a wipe extraction slit 117 that facilitate removal oldie cleanup wipe from the pouch. The diaper disposal aid pouch can be made of a disposable material like that of the outer surface of diaper itself, i.e. a plastic or polymer material such as polyethylene. The removal of the cleaning wipe and the disposal bag from the respective pouches is shown in FIG. 2.

The disposal bag is fixed to the inside of the containment pouch at one end in order facilitate easier insertion of the used diaper into the bag (i.e. by placing one's hand into the bag, grabbing the diaper and pulling it reverse the bag). The free end of the disposal bag 114 is connected to and accessed by the bag pull tab 112 which protrudes out of the bag compartment 115 through the bag extraction slit 113, whereas the other end of the disposal bag is fixed to the inside of the bag compartment 115. In the same way, the disposable cleaning wipe 119 is connected to and accessed by the wipe pull tab 118 which protrudes out of the wipe compartment 116 through the wipe extraction slit 117. However, unlike the bag, the cleaning wipe is not fixed to the inside of the pouch, but rather is completely removable, so that it can be used to clean the baby. An advantage of the diaper of the present invention is that the diaper disposal aid 110 can be made separately from the diaper and affixed thereto. In this way, the disposable diaper of the present invention can be made without modifying the manufacturing process for the diaper. Instead, the diaper disposal aid 110 is made separately and simply affixed (e.g. via adhesive) to the diaper body to complete the diaper. Since styles of diaper vary to some degree, the placement and configuration of the diaper disposal aid can be adjusted accordingly. The diaper 130 in FIG. 1 shows a preferred placement of the diaper disposal aid on a standard diaper.

As described above, the cleaning wipe and disposal bag each have a pull tab and are removed from the wipe compartment and bag compartment, respectively, through a slit in their respective compartments. However, other means of removing the contents of the compartments can be utilized while keeping with the spirit of the present invention. For example, instead of a pull tab, an adhesive sticker could cover the extraction slit whereby removing the sticker would expose the slit and allow access to the compartment contents (i.e. the cleaning wipe or disposal bag). An example of such an alternative embodiment is described in connection with FIGS. 4A and 4B below.

Motion arrows 100 and 101 indicate the fastening of the diaper as during placement of the diaper upon the wearer. Via motion arrow 100, a user secures the diaper 130 on the body of the wearer by bringing the upper fastening element 120 (found on the interior surface of the waistband section 126) into contact with the corresponding lower fastening element 125 (found on the exterior surface of the lower fastening element 125 of crotch section 127. The upper fastening element 120 is adjacent to the waistband section 126 of the diaper. The lower fastening element 125 is adjacent to the crotch section 127 of the diaper. These fastening elements are secured upon their contact via standard methods known in the art, such as adhesive or Velcro surfaces. Motion arrow 101 shows the resultant path and destination, of the diaper disposal aid during the aforementioned securing of the diaper denoted by motion arrow 100. The purpose of motion arrow 101 is primarily to illustrate that the diaper disposal aid becomes hidden from view once the diaper is fastened upon the wearer. More specifically, the disposal aid's surface makes contact with a small area adjacent to the lower fastening element 125 near crotch section 127, thus layering it between the waistband section and the crotch section, and making it inaccessible by the wearer (i.e. inaccessible until diaper removal). In this manner, the disposal aid 120 does not make contact with the wearer's skin, is not accessible by the wearer, and cannot become soiled or cause discomfort, which are all important aspects to safe and convenient usage of the disposal aid. Thus, the diaper aid is both safe from access by the wearer, and does not cause discomfort or irritation by contacting the wearer's skin.

FIG. 2 illustrates a perspective view of both disposable cleaning wipe extraction and disposal bag extraction/utilization. The figure depicts a soiled diaper 230 which has been removed from the wearer. Upper fastening element 220 has been detached from or peeled off of lower fastening element 225. In an example of usage, a user may utilize diaper disposal aid 210 by first pulling the wipe pull tab 218 and thereby removing the cleaning wipe 219 from the wipe compartment 216 through the wipe extraction slit 217 as indicated by motion arrow 202. With the cleaning wipe fully extracted from its pouch, it may now be utilized for cleaning the wearer of the diaper as needed. Thereafter, the wipe may be disposed of by placing it in the diaper.

Following use of the wipe, the user can then pull the bag pull tab 212 to remove the disposal bag 214 from the containment pouch 215 through bag extraction slit 213. FIG. 1 shows the removal of the cleanup wipe by a user's left hand 291 as indicated by motion arrow 203. The small portion of the disposal bag remaining within the bag compartment 215 terminates at a bag attachment point 211, anchoring it to the interior of the pouch (via adhesive, stitching or other conventional attachment means). The extracted disposal bag 214 has a bag opening 209 into which a user places their hand (i.e. right hand 290) to grasp the body of the soiled diaper 230 and pull the entire diaper through the bag. This action contains the soiled diaper within the bag by reversing the interior of the bag so that it becomes the exterior. Once a soiled diaper 230 has been contained within the disposal bag 214, the bag may be tied up (sealing the bag opening 209) and/or simply discarded, as desired.

Figure 3:
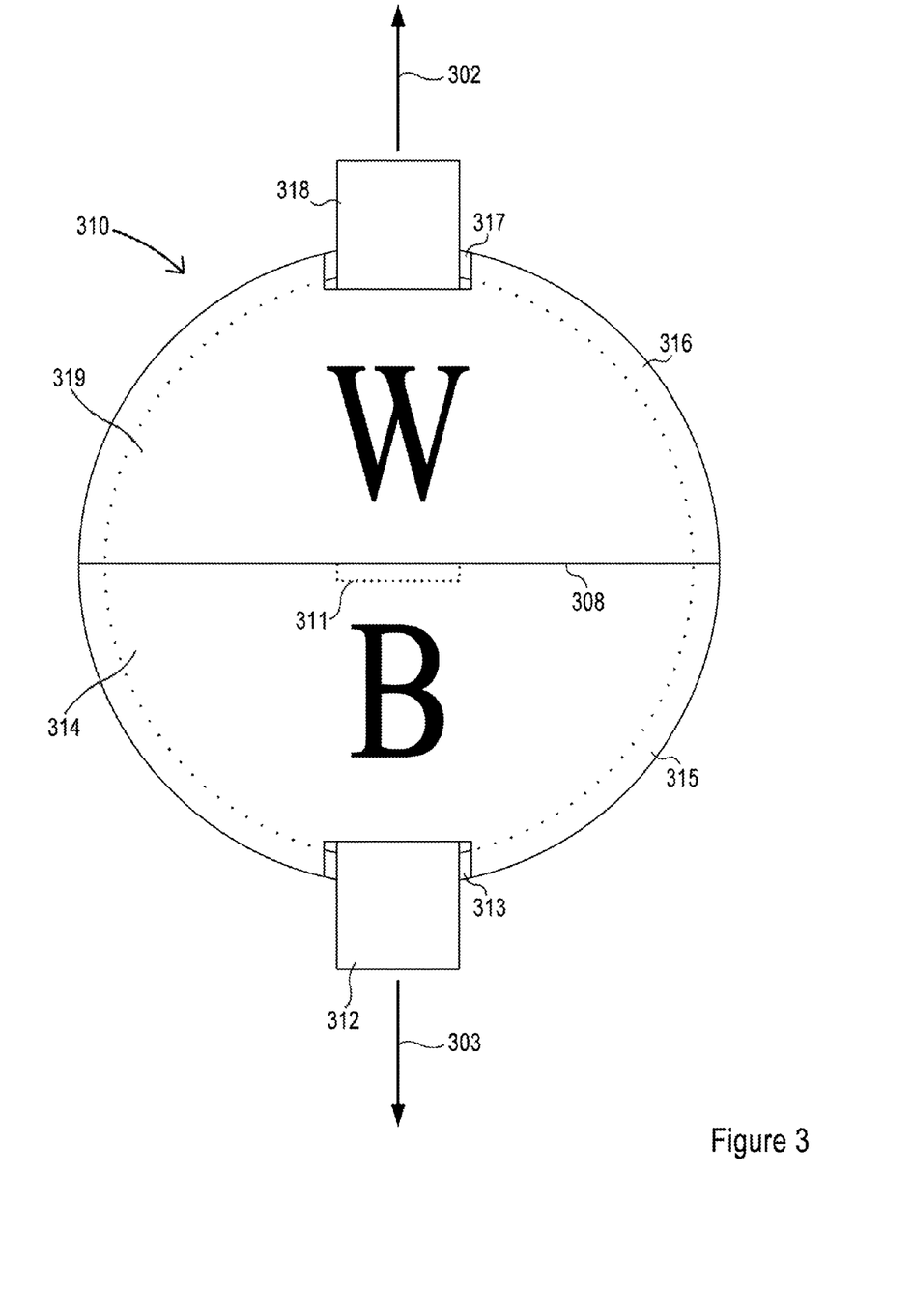
FIG. 3 illustrates a close-up view of the cleanup and disposal aid showing the motion of both the cleaning wipe pull tab and the bag pull tab.

FIG. 3 illustrates a close-up, top view of a diaper cleanup and disposal aid. As discussed above, the disposal aid can be advantageously manufactured in a separate process from that of the diaper and then affixed thereto. The diaper disposal aid 310 comprises a bag compartment 315 (denoted by "B") and a wipe compartment 316 (denoted by "W"). These two pouches are separated by a pouch divider 308. The bag compartment 315 further comprises a disposal bag 314, a bag pull tab 312; and a bag extraction slit 313. The wipe compartment 316 further comprises a disposable cleaning wipe 319, a wipe pull tab 318, and a wipe extraction slit 317. Motion arrow 302 denotes the sliding action of the wipe pull tab 318 which is attached to, and results in the movement of, the disposable cleansing wipe 319 out of the interior of the wipe compartment 316. Similarly, motion arrow 303 denotes the sliding action of the bag pull tab 312 (which is connected to the bag) out from the body of the bag compartment 315 to extract the majority of the disposal bag therefrom. The disposal bag 314 is anchored to the interior bottom edge of the bag compartment 315 via attachment point 311. The cleanup wipe and disposal bag can be stored within their respective pouches via vacuum compression, tight folding, or other means known in the art.

Figure 4A:
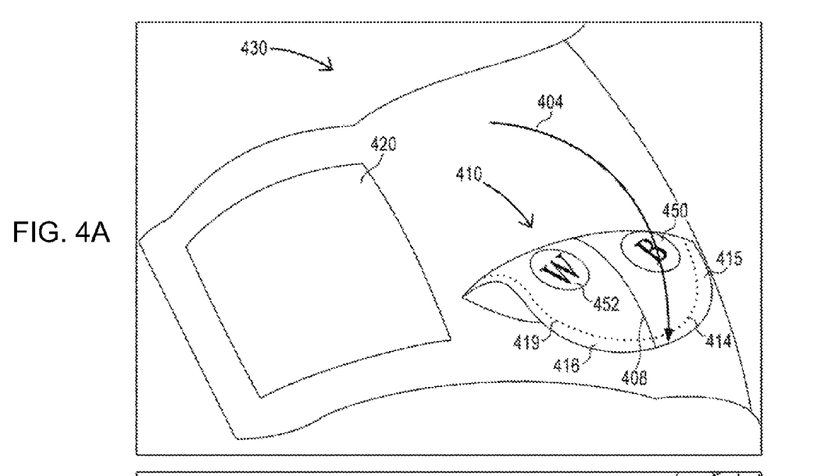
FIGS. 4A and 4B illustrate an alternate embodiment of the diaper disposal aid utilizing a peel away mechanism for extraction of both the disposable cleaning wipe and the disposal bag from the interior of the cleanup and disposal aid.
Figure 4B:
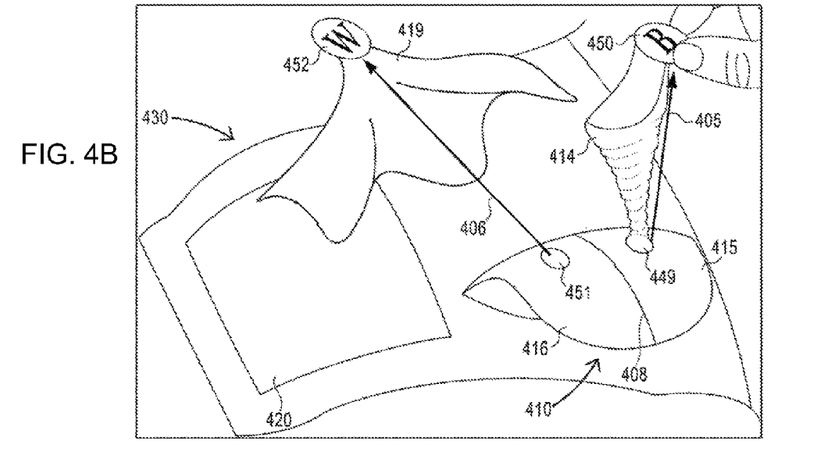

FIGS. 4A and 4B illustrate an alternate embodiment of a diaper disposal aid which presents an alternate means of removing the disposable cleaning wipe and disposal bag from the containment pouch. As in the previous embodiment, the diaper disposal aid 410 comprises two adjoining compartments—a wipe compartment 416 and a bag compartment 415, each separated by the pouch divider 408. As shown in FIG. 4A, unique to this embodiment is the method of first peeling the diaper disposal aid 410 away from the waistband section of the diaper 430 in order to access the contents of the pouch. In this embodiment, the disposal aid 410 is positioned adjacent and interior to the upper fastening element 420. Motion arrow 404 shows the action of peeling away the disposal aid, and consequently revealing the underbelly of the disposal aid (the surface previously adhered to the diaper surface)—which possesses a bag access sticker 450 (shown with a "B" on its surface), and a wipe access sticker 452 (shown with a "W" on its surface). It may be useful to have the disposal aid peel away approximately 75 percent of the sticky portion of its surface from the diaper, thereby leaving it attached to the diaper by a small area for a more streamlined, efficient approach to disposal. This echoes the permanent attachment method of the primary embodiment of the invention. In this embodiment, the disposal aid may be manufactured with the diaper in such a way that it is partially attached in a permanent way to the diaper, e.g. via sewing or alternative method known in the art. As with the primary embodiment, the diaper disposal aid is placed in a location adjacent to upper fastening element 420, obscuring it from view and making it strategically difficult to reach during wearer usage.

FIG. 4B illustrates that, after peeling the disposal aid 410 away from the diaper, a user may grab or pinch the aforementioned access stickers and pull them away (upward in this figure) from the underbelly surface of the disposal aid. With respect to the cleaning wipe 419, this action is carried out via motion arrow 406. Similarly, the disposal bag 414 is extracted via motion arrow 405. Using a method similar to that of the primary embodiment of the invention, the access stickers are attached permanently to their respective sanitation/disposal aids. As such, when (for example) the wipe access sticker 452 is peeled away from its wipe compartment 416, it causes wipe extraction as a secondary consequence. Similarly, when the bag access sticker 450 is peeled away from its bag compartment 415, it causes bag extraction as a secondary consequence. The majority of the bag is extracted through the bag extraction hole 449, which was previously covered by the bag access sticker 450 in FIG. 4A. As in the initial embodiment of the invention, the extracted bag is permanently affixed to the interior of its pouch by an anchor point, whereas the extracted wipe is fully removable from its pouch. Concerning both bag and wipe, the surface of an access sticker that adheres itself to a containment pouch possesses a ring of adhesion surrounding its center—the point at which the bag or wipe is connected. Thus, FIGS. 4A and 4B depict a disposal aid in which the cleaning wipe compartment and disposal bag compartment each contain an opening that is covered by an adhesive tab that can be removed to access the compartment. Moreover, the opening of the cleaning wipe compartment and disposal bag compartment faces the diaper surface such that the disposal aid pouch must be peeled away from the diaper surface in order to access the respective compartments.

Figure 5:
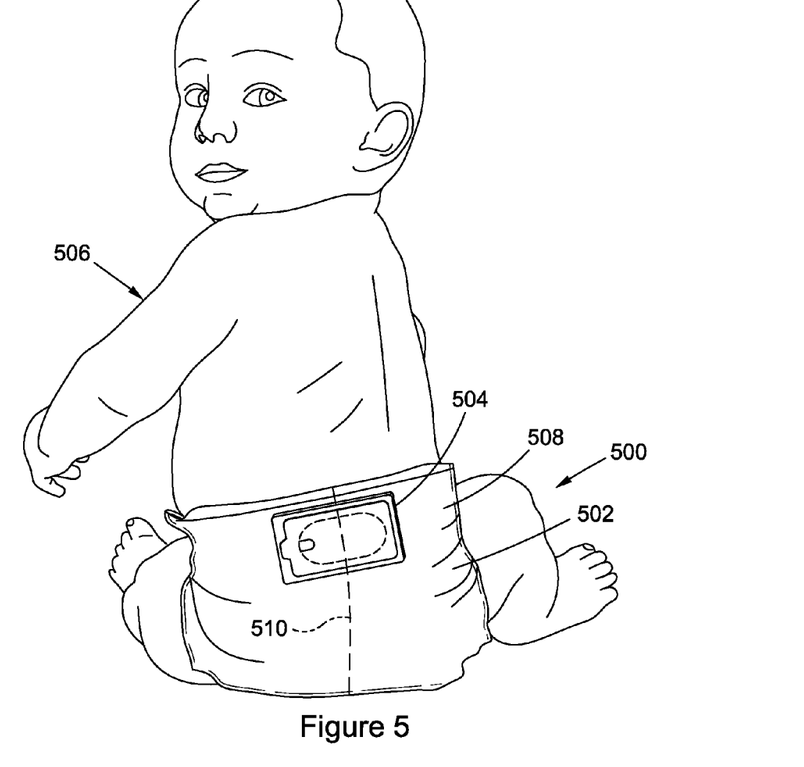
FIG. 5 shows a disposable diaper including a disposal aid worn by an infant according to the present invention.

FIG. 5 depicts a disposable diaper 500 including a diaper body 502 having a waistband region 508, a disposal aid 504 coupled with an exterior surface of the waistband region 508, worn by an infant 506. The waistband region 508 is generally the upper portion of the diaper body 502. In this embodiment, the disposal aid 504 is coupled with the exterior surface of the waistband region 508 about a centerline 510 of the disposable diaper 500 so as to make it difficult for the infant 506 to access or otherwise tamper with the disposal aid 504. The disposal aid 504 is connected to the diaper body 502 via stitches. The diaper body 502 is a standard diaper which may be discarded after one use. The disposal aid 504 is operable to contain a cleaning wipe a disposal bag (not shown) so that the infant 506 may be cleaned with the cleaning wipe and the diaper discarded in the disposal bag.

Figure 6:
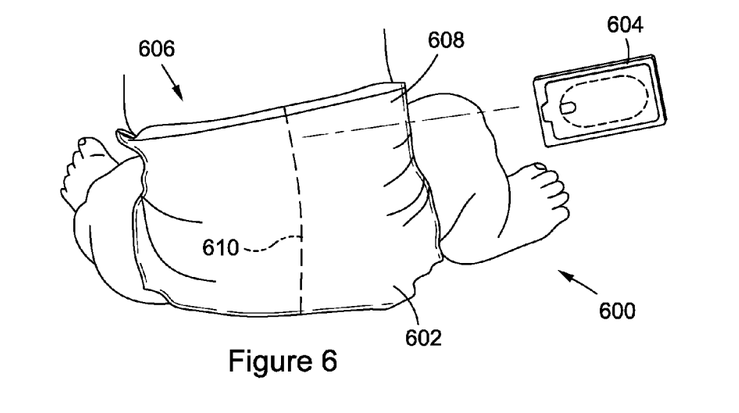
FIG. 6 shows an exploded view of a preferred embodiment of a disposable diaper including a disposal aid which may be coupled with the diaper via an adhesive according to the present invention.

FIG. 6 depicts an exploded view of a preferred embodiment of a disposable diaper 600 including diaper body 602 having a waistband region 608, a disposal aid 604 which may be coupled with an exterior surface of the waistband region 608 via an adhesive (not shown). The adhesive may be natural or synthetic, such as glue. The adhesive can be applied to the bottom surface of the base (not shown) of the disposal aid 604. As such, the disposal aid 604 may be coupled with any diaper regardless of whether or not the diaper is disposable. Additionally, the disposal aid 604 may be adhesively coupled with the exterior surface of the waistband region 608 anywhere the user chooses. Lastly, the user may utilize more than one disposal aid 604 to connect to the diaper body 602.

Figure 7:
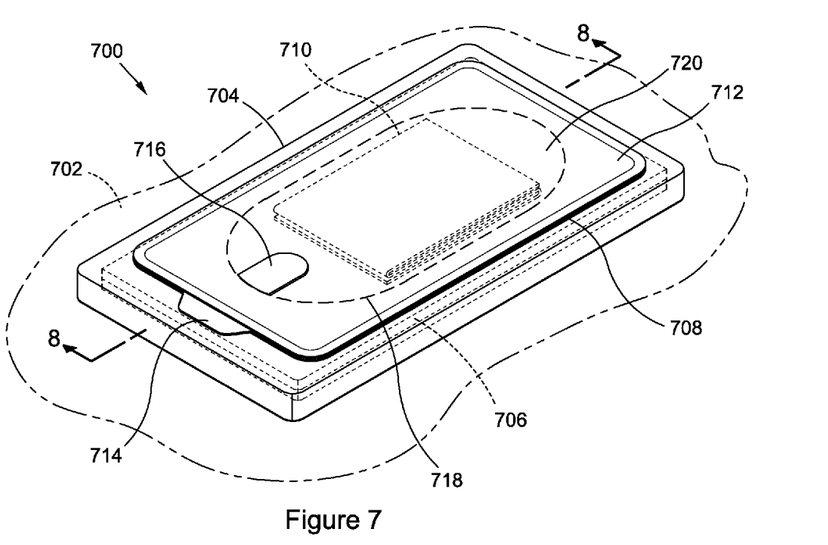
FIG. 7 shows a perspective view of a preferred embodiment of a disposal aid comprising a base, a disposal bag, a cleaning wipe, a first removable cover, and a second removable cover according to the present invention.

FIG. 7 depicts a perspective view of a preferred embodiment of a disposal aid 700 comprising a base 704, a disposal bag 706, a cleaning wipe 710, a first removable cover 708, and a second removable cover 712 according to the present invention. The disposal aid 700 is coupled with an exterior surface of a waistband region 702 of a diaper body. The first removable cover 708 has a first tab 714 which makes it easy to remove the first removable cover 708. In one instance, the first tab 714 is affixed to a distal edge of the first removable cover 708, as shown. The second removable cover 712 has a second tab 716, a perforated section 720, and an elliptical perforation 718 around the perforated section 720. In one instance, the second tab 716 is affixed to a distal edge of the perforated section 720 which makes it easy to remove the second removable cover 712. In another instance, the second removable cover 712 only has the perforated section 720 and the elliptical perforation 718 without including the second tab 716. In this configuration, the user simply presses on the perforated section 720 and it detaches from the second removable cover 712 along the elliptical perforation 718.

As shown in FIG. 7, the disposal aid 700 is a low profile device for containing the disposal bag 706 and the cleaning wipe 710. Although in this figure, the base 704, the first removable cover 708, and the second removable cover 712 are shown to have a rectangular shape, other shapes such as circular and elliptical are contemplated. The base 704 is made from polyethylene. In one instance, the polyethylene is an elastomer which is very flexible and can conform to the shape of the infant's body. The first removable cover 708 and the second removable cover are similarly made from polyethylene and as such are flexible. In one configuration, the base 704 includes a cavity, discussed in more detail below, so as to reduce the overall height of the disposal aid 700.

Figure 8:
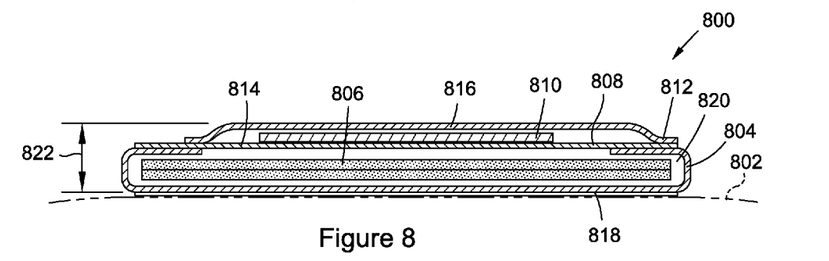
FIG. 8 shows a cross sectional view of a preferred embodiment of a disposal aid comprising a base, a disposal bag, a cleaning wipe, a first removable cover, and a second removable cover according to the present invention.

FIG. 8 depicts a cross sectional view of a preferred embodiment of a disposal aid 800 comprising a base 804, a disposal bag 806, a cleaning wipe 810, a first removable cover 808, and a second removable cover 812 according to the present invention. The disposal aid 800 is coupled with an exterior surface of a waistband region 802 of a diaper body. An adhesive 818 is applied at the bottom of the base 804 to couple the disposal aid 800 to the waistband region 802. In this preferred embodiment, the base 804 comprises a cavity 820 so operable to receive the disposal bag 806 within the cavity 820 so as to reduce the overall height 822 of the disposal aid 800. As in the disposal aid 700 of FIG. 7, the first removable cover 808 has a first tab 814 which makes it easy to remove the first removable cover 808. The second removable cover 812 has a second tab (not shown), a perforated section 816, and an elliptical perforation around the perforated section 816 so as to make it easy to remove the perforated section 816 of the second removable cove 812.

Figure 9:
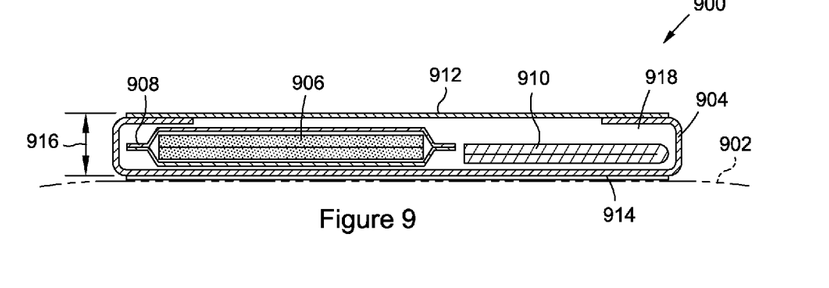
FIG. 9 shows a cross sectional view of a preferred embodiment of a disposal aid comprising a base, a disposal bag, a cleaning wipe and a removable cover according to the present invention.

FIG. 9 depicts a cross sectional view of a preferred embodiment of a disposal aid 900 comprising a base 904, a disposal bag 906 encased in a casing 908, a cleaning wipe 910 and a removable cover 912 according to the present invention. The disposal aid 900 is coupled with an exterior surface of a waistband region 902 of a diaper body. An adhesive 914 is applied at the bottom of the base 904 to couple the disposal aid 900 to the waistband region 902. In this preferred embodiment, the disposal aid 800 includes only the one removable cover 912 which does not include a tab. The base 904 comprises a cavity 918 where both the cleaning wipe 910 and disposal bag 906 and its casing 908 reside. As in the disposal aid 800 of FIG. 8, the cavity 918 is included so as to reduce the overall height 916 of the disposal aid 900. Once the removable cover 912 is removed, both the cleaning wipe 910 and the casing 908 become accessible to the user, thereby, facilitating removal of the casing 908 and the cleaning wipe 910. The casing 908 contains the disposal bag 906 which the user may access by opening the casing 908. In one instance, the casing 908 is made from polyethylene.

Figure 10:
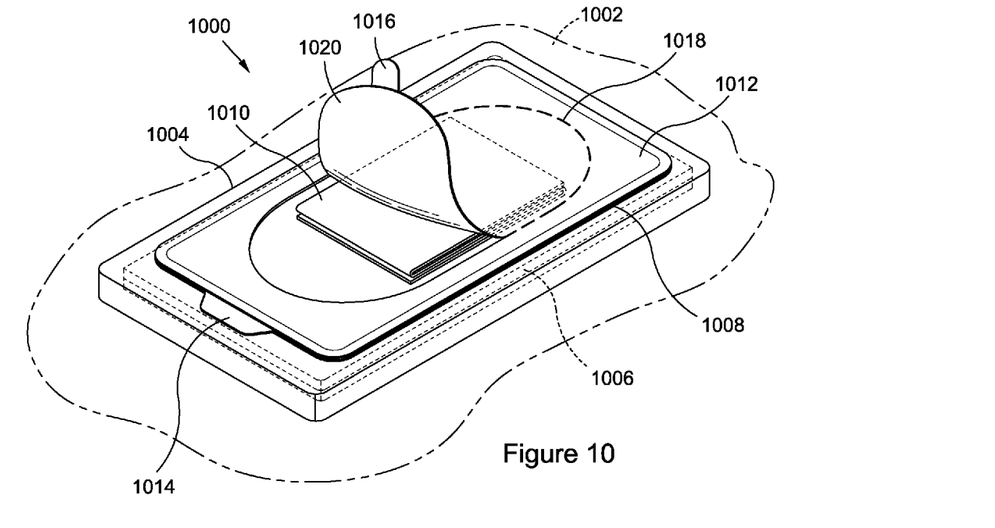
FIG. 10 shows a perspective view of a preferred embodiment of a disposal aid comprising a base, a disposal bag, a cleaning wipe, a first removable cover, and a second removable cover further illustrating how the second removable cover may be removed to access the cleaning wipe according to the present invention.

FIG. 10 depicts a perspective view of a preferred embodiment of a disposal aid 1000 comprising a base 1004, a disposal bag 1006, a cleaning wipe 1010, a first removable cover 1008, and a second removable cover 1012 further illustrating how the second removable cover 1012 may be removed to access the cleaning wipe 1010 according to the present invention. The disposal aid 1000 is coupled with an exterior surface of a waistband region 1002 of a diaper body. The first removable cover 1008 has a first tab 1014 which makes it easy to remove the first removable cover 1008. The second removable cover 1012 has a second tab 1016, a perforated section 1020, and an elliptical perforation 1018 around the perforated section 1020 so as to make it easy to remove the perforated section 1020 of the second removable cove 1012.

Figure 11:
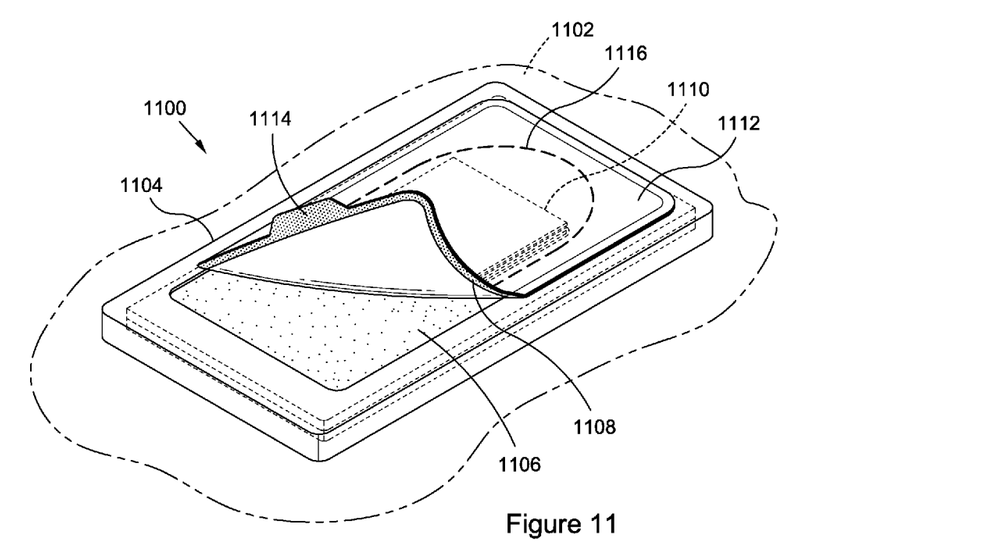
FIG. 11 shows a perspective view of a preferred embodiment of a disposal aid comprising a base, a disposal bag, a cleaning wipe, a first removable cover, and a second removable cover wherein the second removable cover has been removed, further illustrating how the first removable cover may be removed to access the disposal bag according to the present invention.

FIG. 11 depicts a perspective view of a preferred embodiment of a disposal aid 1100 comprising a base 1104, a disposal bag 1106 and a cleaning wipe 1110 which is shown in dotted line to indicate that it has been accessed by the user and removed. The disposal aid 1100 further comprises a first removable cover 1108 and a second removable cover 1112 which includes a perforation 1116 around a perforated section which has been removed, further illustrating how the first removable cover 1108 may be removed to access the disposal bag 1106 according to the present invention.

Figure 12:
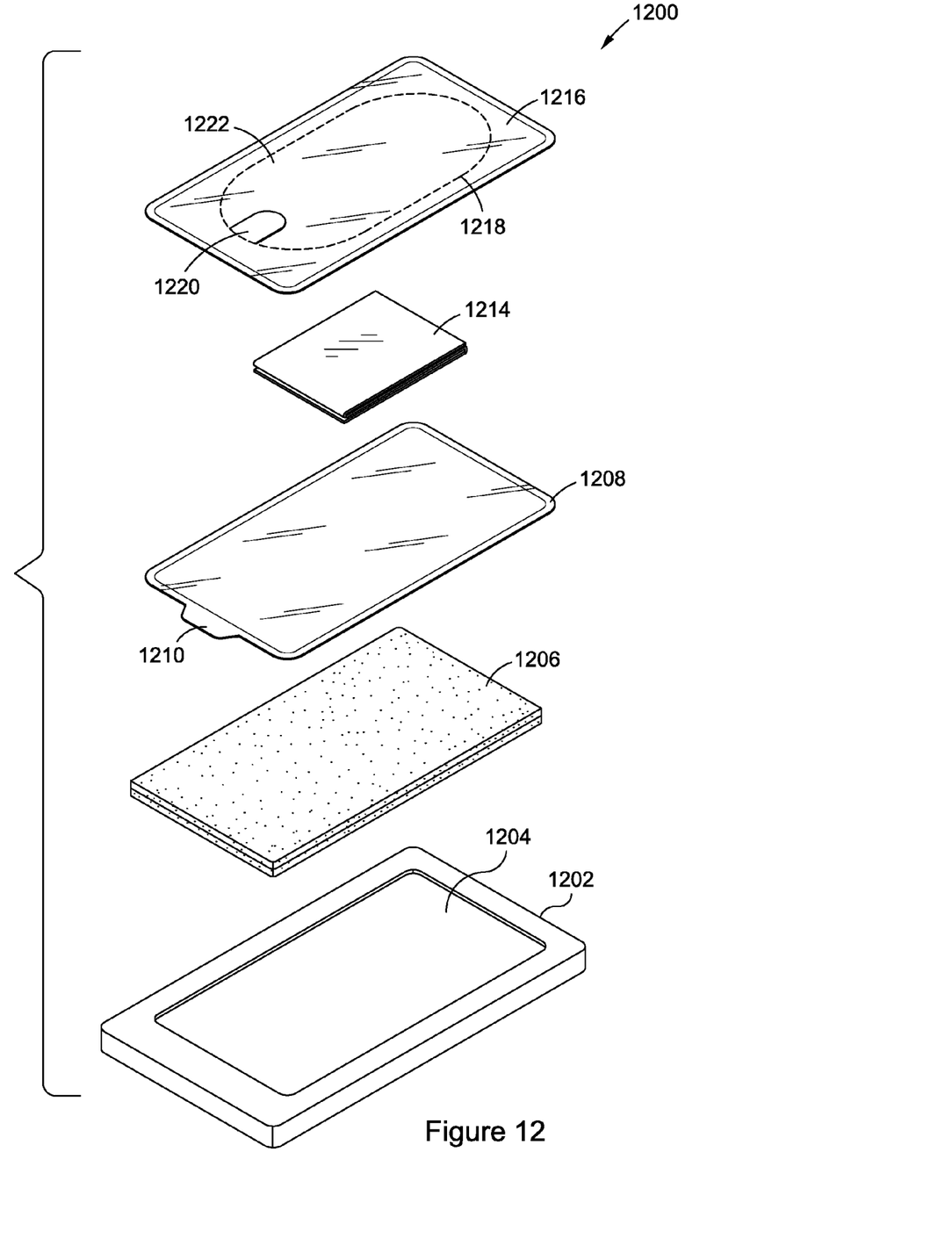
FIG. 12 shows an exploded view of a preferred embodiment of a disposal aid comprising a base, a disposal bag, a cleaning wipe, a first removable cover, and a second removable cover further illustrating how the different components of the disposal aid may be sandwiched together according to the present invention.

FIG. 12 shows an exploded view of a preferred embodiment of a disposal aid 1200 comprising a base 1202 which has a cavity 1204, a disposal bag 1206, a cleaning wipe 1214, a first removable cover 1208 which has a first tab 1210, and a second removable cover 1216 which has a second tab 1220, a perforated section 1222 and an elliptical perforation 1218 around the perforated section 1222, further illustrating how the different components of the disposal aid 1200 may be sandwiched together in order to reduce the overall height of the disposal aid 1200 according to the present invention. In this preferred embodiment, the base 1202 is made from an elastomer rendering the disposal aid 1200 conformable to the shape of a disposable diaper when worn by an infant.

The foregoing explanations, descriptions, illustrations, examples, and discussions have been set forth to assist the reader with understanding this invention and further to demonstrate the utility and novelty of it and are by no means restrictive of the scope of the invention. It is the following claims, including all equivalents, which are intended to define the scope of this invention.

What is claimed is:

1. A disposable diaper, comprising:
   (a) a diaper body comprising a waistband region;
   (b) a disposal aid coupled with an exterior surface of the waistband region, said disposal aid, comprising:
   (i) a base operable to contain a cleaning wipe and a disposal bag:
   (ii) a first removable cover removably affixed to the base, capable of being completely removed from the base, and operable to cover the disposal bag and to facilitate a platform to place the cleaning wipe thereon; and
   (iii) a second removable cover removably affixed to the first removable cover, capable of being completely removed from the first removable cover, and operable to cover the cleaning wipe;
   wherein by removing the second removable cover, the cleaning wipe becomes accessible, thereby, facilitating removal of the cleaning wipe; and
   wherein by removing the first removable cover, the disposal bag becomes accessible, thereby, facilitating removal of the disposal bag.

2. The disposable diaper of claim 1, wherein the disposal aid is coupled with the exterior surface of the waistband region via an adhesive.

3. The disposable diaper of claim 1, wherein the disposal aid is coupled with the exterior surface of the waistband region and disposed about a centerline of the disposable diaper.

4. The disposable diaper of claim 1, wherein the base is made of polyethylene.

5. The disposable diaper of claim 1, wherein the base is rectangular.

6. The disposable diaper of claim 1, wherein the first removable cover and the second removable cover are rectangular.

7. The disposable diaper of claim 1, wherein the base comprises a cavity operable to receive the disposal bag within said cavity, thereby reducing an overall height of the disposal aid.

8. The disposable diaper of claim 1, wherein the first removable cover includes a first tab affixed to a distal edge of the first removable cover thereby facilitating easy removal of the first removable cover, and wherein the second removable cover includes a second tab affixed to a distal edge of a perforated section of the second removable cover and an elliptical perforation around the perforated section, thereby facilitating easy removal of the perforated section of the second removable cover.

9. A disposable diaper, comprising:
   (a) a diaper body comprising a waistband region;
   (b) a disposal aid coupled with an exterior surface of the waistband region, said disposal aid, comprising:
   (i) a base operable to contain a cleaning wipe and a disposal bag:
   (ii) a casing operable to encase the disposal bag; and (iii) a removable cover removably affixed to the base, capable of being completely removed from the base, and operable to cover the casing and the cleaning wipe;
wherein by removing the removable cover, the casing and the cleaning wipe become accessible, thereby, facilitating removal of the casing and the cleaning wipe.

10. The disposable diaper of claim 9, wherein the base is rectangular.

11. The disposable diaper of claim 9, wherein the removable cover is rectangular.

12. The disposable diaper of claim 9, wherein the base comprises a cavity operable to receive the disposal bag and the cleaning wipe within said cavity, thereby reducing an overall height of the disposal aid.

13. The disposable diaper of claim 9, wherein the removable cover includes a tab affixed to a distal edge of the first removable cover thereby facilitating easy removal of the first removable cover.

14. A disposal aid configured to be coupled with an exterior surface of a diaper, comprising:
(i) a base operable to contain a cleaning wipe and a disposal bag:
(ii) a first removable cover removably affixed to the base, capable of being completely removed from the base, and operable to cover the disposal bag and to facilitate a platform to place the cleaning wipe thereon; and
(iii) a second removable cover removably affixed to the first removable cover, capable of being completely removed from the first removable cover, and operable to cover the cleaning wipe;
wherein by removing the second removable cover, the cleaning wipe becomes accessible, thereby, facilitating removal of the cleaning wipe; and
wherein by removing the first removable cover, the disposal bag becomes accessible, thereby, facilitating removal of the disposal bag.

15. The disposal aid of claim 14, wherein the base is rectangular.

16. The disposal aid of claim 14, wherein the first removable cover and the second removable cover are rectangular.

17. The disposal aid of claim 14, wherein the base comprises a cavity operable to receive the disposal bag within said cavity, thereby reducing an overall height of the disposal aid.

18. The disposal aid of claim 14, wherein the first removable cover includes a first tab affixed to a distal edge of the first removable cover thereby facilitating easy removal of the first removable cover, and wherein the second removable cover includes a second tab affixed to a distal edge of a perforated section of the second removable cover and an elliptical perforation around the perforated section, thereby facilitating easy removal of the perforated section of the second removable cover.

19. A disposal aid configured to be coupled with an exterior surface of a diaper, comprising:
(i) a base operable to contain a cleaning wipe and a disposal bag:
(ii) a casing operable to encase the disposal bag; and
(iii) a removable cover removably affixed to the base, capable of being completely removed from the base, and operable to cover the casing and the cleaning wipe;
wherein by removing the removable cover, the casing and the cleaning wipe become accessible, thereby, facilitating removal of the casing and the cleaning wipe.

20. The disposal aid of claim 19, wherein the base comprises a cavity operable to receive the disposal bag and the cleaning wipe within said cavity, thereby reducing an overall height of the disposal aid.

\* \* \* \* \*